United States Patent [19]

Weber

[11] 4,185,387

[45] Jan. 29, 1980

[54] DENTAL ARTICULATOR

[76] Inventor: Roland Weber, 5 Grande-chéne, Lausanne, Switzerland

[21] Appl. No.: 807,238

[22] Filed: Jun. 16, 1977

[30] Foreign Application Priority Data

Oct. 21, 1976 [CH] Switzerland .................... 13299/76

[51] Int. Cl.$^2$ ............................................ A61C 11/00
[52] U.S. Cl. .................................................... 433/61
[58] Field of Search ............................................ 32/32

[56] References Cited

U.S. PATENT DOCUMENTS

| | | | |
|---|---|---|---|
| 2,070,025 | 2/1937 | Phillips | 32/32 |
| 2,535,146 | 12/1950 | Lyons | 32/32 |
| 2,930,127 | 3/1960 | Mann et al. | 32/32 |
| 2,952,914 | 9/1960 | Shackelford | 32/32 |
| 3,078,577 | 2/1963 | Prentki | 32/32 |

FOREIGN PATENT DOCUMENTS 1291854 4/1969 Fed. Rep. of Germany .............. 32/32

*Primary Examiner*—Russell R. Kinsey
*Assistant Examiner*—John J. Wilson
*Attorney, Agent, or Firm*—Miller & Prestia

[57] ABSTRACT

An improved articulator for monitoring and correcting masticatory surfaces of the upper and lower jaw portions of a dental prosthesis model is provided. The improved articulator includes a frame and two reproduction bodies movably mounted on the frame that are respectively designed to carry an upper and lower jaw portion of a dental prosthesis. Articulation means connected to the reproduction bodies move the bodies three-dimensionally in relation to one another to copy the articulative movements of a patient. Compensation means connected to at least one of the reproduction bodies provides three-dimensional adjustment of a jaw model portion in relation to the reproductive body, when the jaw model is attached to the body.

2 Claims, 5 Drawing Figures

DENTAL ARTICULATOR

BACKGROUND OF THE INVENTION

1. Field of the Invention

The present invention relates to an improved articulator of the type designed to grind in the masticatory surfaces of an upper and lower jaw portion of a dental prosthesis model. More specifically, in an articulator of the type having two reproduction bodies, each three-dimensionally movable in relation to the other to copy a patient's articulative movements, the improvement includes compensation means connected to one of the reproduction bodies to provide three-dimensional adjustment of a jaw model in relation to the reproduction body.

2. Description of the Prior Art

The movements of a set of teeth, whether a natural set, one provided with bridges and inserted teeth, or one consisting of dental prostheses, are composed of the articulation movements of the lower jaw and, in the case of an artificial denture, of the individual movements of the prostheses support structures elastically fitted on the mucuous membrane. An exact three-dimensional measurement and recording of these composite movements and the most complete possible simulation of these movements on an articulator are absolutely necessary in order to render possible grinding in of the masticatory surface relief in such a way that incorrect settings and temporary or permanent over-stressing of the temporo-mandibular joints (jaw joints) and especially of the condyles (jaw joint heads) can be excluded. This is particularly important because according to the latest knowledge, the lasting over-stressing of the jaw joints, due to an incorrect position of the lower jaw by reason of a defective occlusion of the jaws, can have far-reaching consequences in the well-being of the person, and can inter alia be the cause of migraine.

Measuring instruments are known wherein the movements of the lower jaw and the exact positions of the parts of the set of teeth of the patient may be recorded. Further, articulators have been provided that cooperate with such measuring instruments to grind in the mastication surface profiles of a set of artificial teeth, wherein the upper and lower jaw models may be articulated with respect to each other to copy the patient's articulative motions. U.S. Pat. No. 3,552,020, of common inventorship herewith, describes such an articulator wherein the movements of the lower jaw in relation to the upper jaw can be copied practically perfectly.

This known articulator, which is acknowledged by science and is already used by dentists, despite all the advantages which it offers in relation to the reproducibility of the masticatory movements, still possesses a disadvantage which should not be underestimated. This consists in that as a result of uncontrollable plaster expansion, the jaw model is moved out of its correct position during the setting of the plaster that connects its base with the associated part of the articulator. Accordingly, the occlusion on the articulator is no longer in conformity with the effective occlusion measured on the patient, or the condyle positions on the articulator differ from the actual positions of the jaw joints in the patient. Thus, certain masticatory surface profile errors, even though slight, are unavoidable.

Therefore, it is an object of the present invention to provide an improved articulator wherein inaccuracies due to the setting of the jaw plaster models can be compensated and corrected, in order to precisely reproduce the jaw movements of the patient to guarantee a perfect reproduction of the occlusion conditions on the articulator.

SUMMARY OF THE INVENTION

This and other problems inherent in the known art are solved by the present invention. Basically, the articulator comprises a frame with two reproduction bodies movably mounted thereto that are adapted to carry an upper and lower jaw model respectively. The reproduction bodies are connected with articulation means by which each of the bodies is three-dimensionally adjustable in relation to the other reproduction body.

Further, each of the bodies is provided with means for mounting one of the jaw models thereto, and at least one of the bodies is provided with compensation means that provide three-dimensional adjustment of the associated jaw member in relation to the reproduction body.

The compensation means include a compensation plate that is interposed between the reproduction body and the jaw model. Set screws or the like engage both the reproduction body and the compensation plate, and provide a mechanism whereby the inclination of the plate to the body can be easily adjusted. Further, a tube member attached to the reproduction body is disposed within an annular space defined by a ring member attached to the compensation plate with the longitudinal axis of the tube being perpendicular to a generally horizontal plane passing through the ring. A second set of set screws extends through the ring to abut the tube. Accordingly, the axis of the tube may be adjusted with respect to the axis of the ring upon the manipulation of the set screws, so that the reproduction body and compensation plate may be moved laterally in relation to each other.

In another embodiment, the jaw model is firmly attached to a magnetic plate that is magnetically attracted to the compensation plate. In this manner, the jaw model can be easily detached from the reproduction body.

The invention is further explained in conjunction with the following description of the drawings and detailed description.

DETAILED DESCRIPTION

Figure 1:
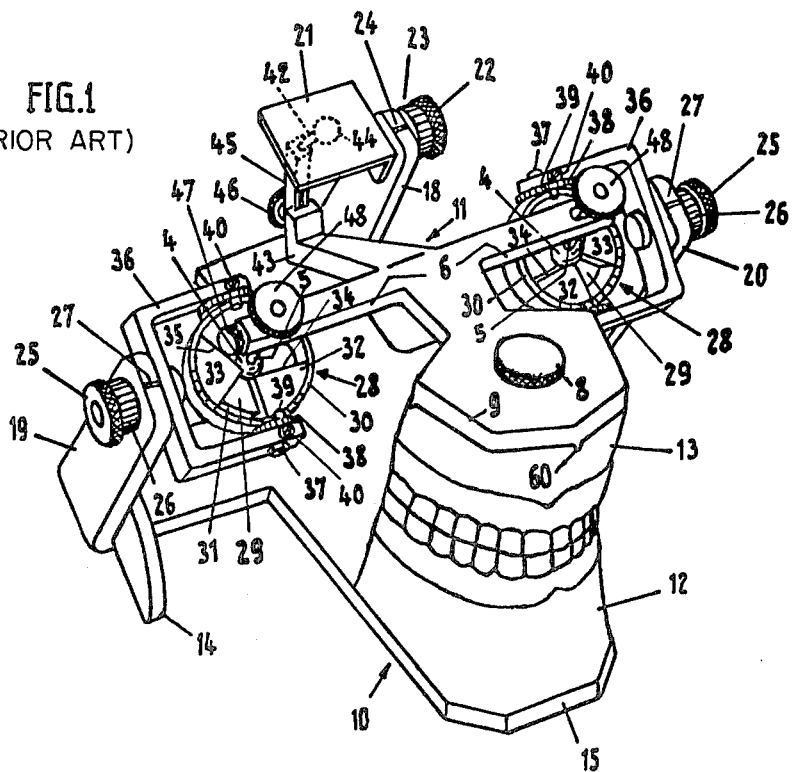
FIG. 1 is a perspective view of a known prior art articulator that may be provided with compensation means in accordance with the present invention.
Figure 2:
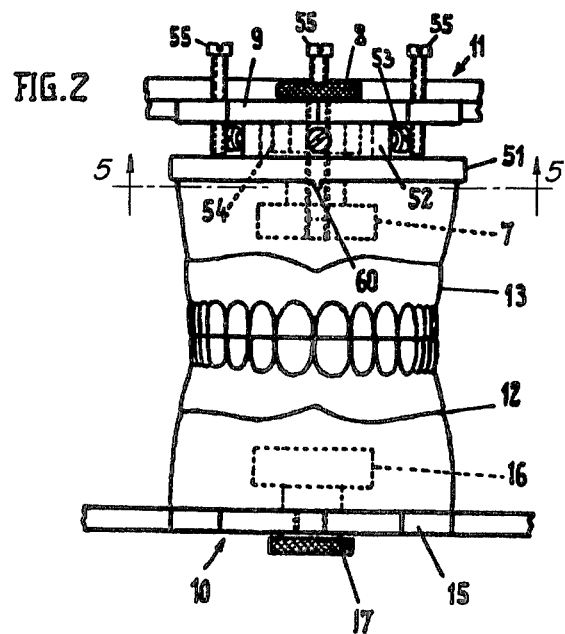
FIG. 2 is a partially cut away front elevational view of the reproduction bodies shown in the FIG. 1 apparatus, but provided with one embodiment of compensation means in accordance with the present invention.

With reference to FIG. 1 of the drawings, there is shown an articulator of the type disclosed in U.S. Pat. No. 3,552,020, of common inventorship herewith. The articulator consists of a lower part 10 and an upper part 11 which are separate and are equipped to carry the lower and upper jaw models 12 and 13 respectively. For this purpose the lower part 10 has on a cruciform foot 14 a carrier plate 15 on which the lower jaw model 12 is detachably secured by means of a nut 16 plastered into the model, with a screw 17 (FIG. 2). The foot 14 is bevelled to the rear so that the lower part 10 can be set up in an appropriate oblique position. On the lower part 10 a rear support arm 18 at the foot end and two lateral support arms 19 and 20 extend upwardly as carriers of three guide devices for the guidance of the upper part.

The guide device on the upper end of the rear support arm 18 consists of a guide plate 21 which has a flat guide surface and is pivotable with a horizontal pivot spindle arranged on it and passing through the support arm 18 and can be secured on the support arm 18 by means of a locking nut 22 screwed onto the free end of the pivot spindle. A scale ring 23 rotating with the pivot spindle renders it possible to read off the inclination of the guide surface against a marking line 24 on the support arm 18.

The other two guide devices are mounted on the upper end of one each of the two lateral support arms 19 and 20 for pivoting about a common geometric axis in the same manner by means of a pivot spindle 41 each, and can be clamped fast on the associated support arm 19 or 20 each by means of a locking nut 25 screwed on to the free end of the pivot spindle 41. A scale ring 26 rotating with the pivot spindle 41 renders it possible to read off the set inclination of the guide device as a whole by a marking line 27 on the support arm. Each of these two guide devices has a circular plate 28 having a flat guide surface 29 and an annular edge 30 protruding thereabove. Between the guide surface 29 and the annular edge 30 an annular groove 31 is provided which due to the undercutting extends below the guide surface 29 and in which two guide segments 32 and 33 are pivotable about the axis of the circular plate 28, which is perpendicular to the guide surface, and can be locked each by means of a screw in any setting. Each segment 32 and 33 possesses a flat guide surface 34 and 35 respectively, each surface being perpendicular to the guide surface 29. The surfaces, in every position of the segment, have an invariable space R from the axis of the circular plate, while a second defining surface of the segment 32 or 33, at right angles to the guide surface 34 and 35, lies in each case in an axial plane of the circular plate 28.

Each plate 28 is pivotably mounted on the legs of a U-shaped frame 36, the middle part of which is secured to the pivot spindle 41, for pivoting by means of two journals 37 about an axis which extends parallel above the guide surface 29 and is at the same distance R therefrom as the guide surfaces 34 and 35 of the segments from the circular plate axis. Journals 37 are disposed at right angles to the pivot spindles 41. The journals 37 can be axially adjustable in the legs, in order that the circular plate may be shifted to a slight extent in this axial direction.

The adjustment of the segment guide surfaces 34 and 35 on the circular plate 28 can be read off by means of defining surfaces on a scale provided on the plate edge 30. Likewise, the oblique position of the plate guide surface 29 in relation to the frame 36 can be read off against a marking line on the frame legs by means of two scale discs rotatably arranged on the journals 37 between the plate 38 and the adjacent frame leg. The scale discs 38 each have for cooperation with the circular plate 28 an axially parallel stop pin 39 which can be brought to abut the circular plate edge 30. The scale discs 38, with stop pins 39, are rotatable about the journals 37 and can be secured by means of locking nuts 40 screwed onto the respective journal portions 37.

Each of the two pivot spindles 41 has at its end directed towards the plate 28 a coaxial recess in the end face for the partial reception of a ball head of a known measuring device for recording the individual chewing movements. Such a measuring device is disclosed in my prior U.S. Pat. No. 3,552,020.

To carry the upper jaw model 13, the upper part 11 of the known articulator has a substantially cruciform carrier on whose forward leg, forming a base plate 9, the upper jaw model 13 is detachably secured by means of a headed screw 8 and a nut 7 (FIG. 2). At the free end of the rear leg 43 of the upper part 11 a screw shank 42 is provided with a hemispherical head 44 protruding against the guide surface of the guide plate 21, which head is intended to cooperate with the guide surface in order to achieve what is called the rear bite guidance. The radius of the spherical head is equal to the distance of the pivot axis of the scale ring 23 from the guide surface and the sphere centre lies in the vertical central plane of the upper part of the articulator.

On the legs 6 extending to both sides on the upper part 11, parallel with the vertical central plane, there are fitted two arms 5 which are three-dimensionally adjustable by means of screws 47 and the nuts 48. Arms 5 each carry a spherical head 4 on their free end which are directed against the circular plates 28, in order to cooperate with their guide surfaces 29 and the guide surfaces 34 and 35 of the segments 32 and 33. R in this instance is the radius of the spherical head 4.

The spherical head 44 is secured with its screw shank 42 on an arcuate slide piece 45 which is fitted on the leg 43 for pivoting about the axis (condyle axis) passing through the centre of the two spherical heads 44, and is lockable by means of a clamping screw 46. With this setting device it is possible to carry out corrections of bite level, the setting of the slide piece 45 being readable on a scale against a marking line provided on the leg. The distance of the pivot or rotation axis of the rear bite guide plate from the parallel pivot spindle 41 of the plates 28 and frames 36 is set to the same value as the distance of the condyle axis from the center of the central incisor teeth, whereby every variation of bite level can be read off in actual magnitude.

The setting of the guide members of this known articulator by reference to the recordings effected with the associated and likewise known measuring appliance is known, and can be studied in the aforementioned U.S. Pat. No. 3,552,020.

FIG. 2 shows a partially cut-a-way front elevational view of an articulator according to the invention which conforms in essential parts with the above-described known articulator. In accordance with the invention, compensation means are inserted between the one reproduction body, i.e. the upper part 11, and the associated jaw model, here the upper jaw model 13. These means advantageously consist on the one hand of a compensation plate 51 which is connected firmly with a centering ring 52. The latter carries three centering screws 53, advantageously mutually staggered by 120° in each case. The compensation means also includes centering tube 54 connected with the reproduction body or the plate 9 of the upper part 11, and three regulating screws 55 arranged in an isosceles or equilateral triangle in the upper part 11. These various parts 51-55 here cooperate so that by means of the regulating screws 55, the inclination of the compensation plate 51 in relation to the base plate 9 can be micrometrically adjusted. By means of centering tube 54 arranged within the centering ring 52 and the centering screws acting thereon, the position of the axis of the centering tube 54 in relation to the axis of the centering ring 52 can be micrometrically displaced.

Figure 3:
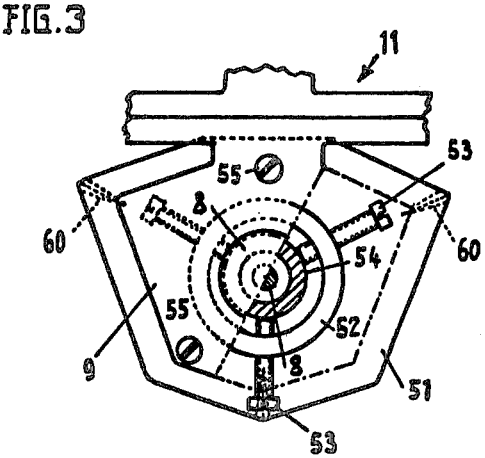
FIG. 3 is a top view, with certain parts cut away for clarification, of the embodiment shown in FIG. 2.

In the embodiment shown in FIGS. 2 and 3, the centering tube is attached to the base plate 9 and is disposed within centering ring 52 with the longitudinal axis of the tube being perpendicular to, and projecting into, the horizontal plane defined by the bores drilled in the centering ring.

The compensation means are held together by the threaded engagement of the screw 8 with the nut 7 cast in the plaster upper jaw model 13. At the same time however, the upper jaw model 13 is thereby three-dimensionally adjustable in relation to the base plate 9. Any expansion of plaster during the setting process or any inaccuracy in the modeling of the jaw models can thus be compensated most precisely. Accordingly, the occlusion on the articulator in accordance with the invention can be adjusted in detail to copy the effective conditions in the patient.

FIG. 3 is a partially cut-a-way top view showing the horizontal adjustability of the compensation plate 51. It may easily be seen from this Figure that by means of the three centering screws 53 the axis of the centering tube 54 can be displaced as desired and deliberately in relation to the axis of the centering ring 52 within limits fixed by the construction of these parts. Within these limits, every predetermined position of the centering tube 54 in relation to centering ring 52 can be precisely set and fixed. It is worthy of mention that this position can be re-found even if the centering ring 52 or the compensation plate 51 with which this ring is firmly connected has been separated from the centering tube 54 or from the base plate 9. This is effected by simple pushing of the centering ring 52 onto the centering tube 54 again. It is naturally a prerequisite here that none of the centering screws 53 have meanwhile been displaced.

Figure 4:
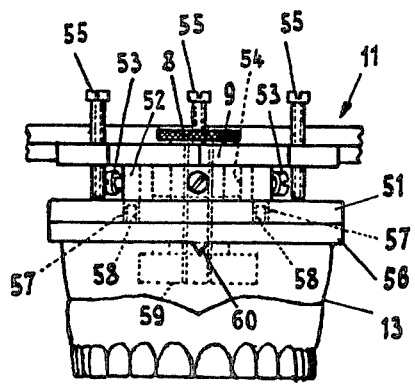
FIG. 4 is a partially cut away front elevational view of the upper reproduction body shown in the FIG. 1 apparatus, but provided with another embodiment of the compensation means in accordance with the present invention.

FIG. 4 shows another embodiment of the novel compensation means in accordance with the invention. This embodiment differs from the embodiment shown in FIGS. 2 and 3 in that compensation plate 51 is not connected directly with upper jaw model 13, but formed as a magnetic plate to which an additional magnetic plate 56 firmly connected with the upper jaw model 13 is attracted. Due to this development of the invention, the handling of the articulator is simplified.

In order that an exact and reproducible position corresponding to the relative disposition of magnetic plate 56 to compensation plate 51 is obtained, (the position of which is defined by means of screws 53 and 55 and by centering ring 52 and centering tube 54) compensation plate 51 is advantageously provided with two or three bores 57 into which pins 58 fit without play.

Assuming that one end of each of the centering screws 53 abuts the centering tube 54, the upper jaw model 13 with magnetic plate 56, firmly connected therewith by means of screw 59, can be separated from the base plate 9 without movement of the compensation plate 51.

Figure 5:
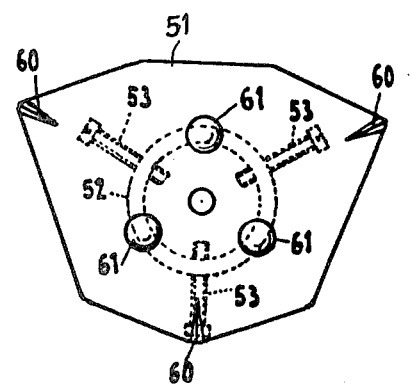
FIG. 5 is a sectional view, with certain parts cut away for clarification, taken along the plane 5—5 of FIG. 2.

FIG. 5 is a sectional view taken along the plane 5—5 of FIG. 2. In this embodiment, after separation of upper jaw model 13 from base plate 9, and thus from compensation plate 51, the jaw model can be placed into the exact position on the compensation plate that it previously occupied. In this embodiment, the compensation plate 51 is advantageously provided with positioning means such as keys 60 that protrude from the underside portion of compensation plate 51. These keys can be repeatedly fitted into the depressions which they have formed in the plaster of the upper jaw model during its setting. Rivet heads 61 which secure centering ring 52 on the compensation plate 51, can also serve the same purpose.

It is self-evident that the embodiment of the invention shown in FIG. 4 does not require the above-described elements 60 or 61 for an exact positioning of upper jaw model 13 on compensation plate 51.

The person acquainted with the art easily recognizes that the invention is not limited to the embodiments as described above. The invention can also be practiced by varying constructions, all without departing from the scope of the invention. Along these lines, the compensation means can also be connected with the other reproduction body, that is, with the lower part 10. It is moreover possible to connect lower jaw model 12, with the lower reproduction body 10 by means of a magnetic plate and positioning means 56, 58. The elements functioning as positioning means for the jaw models 13, 12, (keys, 60 and rivet heads 61) can also be replaced by any desired other expedient means. For this purpose, the compensation plate can, for example, be provided with pins which extend into holes in the plaster jaw model.

It is obvious that the compensation means, as described, can also be connected with reproduction bodies of an articulator which in detail is of different construction than that shown in FIG. 1. Moreover, the shaping of compensation plate 51, and also of plate 56, can be adapted to the existing conditions of the articulator and of the reproduction bodies. Compensation plate 51 (in the case of the embodiment shown in FIG. 3) centering ring 52, and centering tube 54 can be manufactured from synthetic plastic material. In this case, compensation plate 51 and centering ring 52 can be made in one piece. It is also possible to utilize other materials for the production of these elements. According to the material used, it can be advantageous to select self-locking screws as regulating and/or centering screws 55 and 53, in order to prevent unintentional displacement of the position of compensation plate 51. To increase the accuracy of the setting, these screws can also have a micrometer threading.

As emphasized above, the invention offers a great advantage over the articulators ordinarily used hitherto for the gnathological-functional articulation analysis and the resultant adaptation of the masticatory surface profiles, since the conditions in fact present in the patient can be precisely copied and set not only with respect to the movement conditions but also with respect to the occlusion condition. This is by virtue of the three-dimensional micrometric correction and compensation possibilities offered by the articulator according to the invention, which are expressed in the fact that the jaw model or models can be brought three-dimensionally into every desired position of biting, in relation to the condyles. Moreover, due to the present invention, jaw models can be separated from the articulator and subsequently returned to their original position without requiring new setting work. This fact is evidence of still another advantage of the improved articulator disclosed herein.

What is claimed is:

1. An articulator of the type for monitoring and correcting the masticatory surfaces of an upper jaw and a lower jaw dental prosthesis model comprising:
   (a) a frame;
   (b) two reproduction bodies mounted on said frame;
   (c) mounting means for attaching a jaw model to each of said reproduction bodies;
   (d) articulation means connected to said reproduction bodies for moving said bodies in relation to each other to copy the articulative movements of a patient;
   (e) occlusion compensation means connected to at least one of said reproduction bodies for providing three-dimensional adjustment of a jaw model in relation to said reproduction body when said jaw is attached to said reproduction body, said compensation means including a compensation plate attached to one of said reproduction bodies;
   (f) a base plate attached to one of said reproduction bodies;
   (g) a centering ring attached to said compensation plate and having a plurality of threaded bores therein located about a horizontal plane of said ring;
   (h) a centering tube attached to said base plate and disposed within said centering ring with the longitudinal axis of said tube being perpendicular to, and projecting into, the horizontal plane defined by said bores; and
   (i) a plurality of centering screws threaded through said bores, one end of each of said screws abutting said centering tube so that the axis of said tube may be adjusted with respect to the axis of said ring upon reciprocation of said screws within their respective threaded bores.

2. An articulator as recited in claim 1 wherein said reproduction body and attached base plate have a plurality of registering threaded bores formed therein, and further including a plurality of second set screws threaded through said registering bores, one end of each of said second set screws abutting said compensation plate to adjustably regulate the inclination of said compensation plate relative to said base plate.

* * * * *